(12) United States Patent
Vartiainen et al.

(10) Patent No.: US 10,898,147 B2
(45) Date of Patent: *Jan. 26, 2021

(54) ADJUSTABLE LOWER SHELF ON AN X-RAY UNIT

(71) Applicant: PaloDEx Group OY, Tuusula (FI)

(72) Inventors: Sami Vartiainen, Vantaa (FI); Jorma Savolainen, Helsinki (FI); Markku Huovinen, Riihimäki (FI); Wycliffe Raduma, Espoo (FI); Antti Korpela, Kerava (FI); Antti Karhunen, Helsinki (FI); Markus Rintamäki, Tuusula (FI); Juho Malin, Lahela (FI); Saku Leponokka, Riihimäki (FI); Kari Läikkö, Vantaa (FI)

(73) Assignee: PaloDEx Group Oy, Tuusula (FI)

( * ) Notice: Subject to any disclaimer, the term of this patent is extended or adjusted under 35 U.S.C. 154(b) by 181 days.

This patent is subject to a terminal disclaimer.

(21) Appl. No.: 15/952,559

(22) Filed: Apr. 13, 2018

(65) Prior Publication Data

US 2019/0313988 A1  Oct. 17, 2019

(51) Int. Cl.
*A61B 6/14* (2006.01)
*A61B 6/00* (2006.01)
(Continued)

(52) U.S. Cl.
CPC ............... *A61B 6/14* (2013.01); *A61B 6/032* (2013.01); *A61B 6/0478* (2013.01); *A61B 6/4476* (2013.01)

(58) Field of Classification Search
CPC ......... A61B 6/032; A61B 6/0478; A61B 6/14; A61B 6/4441; A61B 6/4476; A61B 6/501; A61B 6/589; A61B 6/4452; A61B 1/00009; A61B 1/00016; A61B 1/0002; A61B 1/00193; A61B 1/051; A61B 1/0638; A61B 1/0684; A61B 1/24; A61B 2576/00; A61B 5/0035; A61B 5/0066; A61B 5/0088; A61B 6/04; A61B 2017/00199; A61B 2017/00477; A61B 2034/305; A61B 2090/508; A61B 34/30; A61B 34/70; A61B 90/50; A61B 6/0407; A61B 6/4007; A61B 6/4266; A61B 6/4085; A61B 6/035; A61B 6/08; A61B 6/447; A61B 6/482; A61B 6/505; A61B 6/5211; A61B 6/025; A61B 6/027; A61B 6/0421; A61B 6/145;
(Continued)

(56) References Cited

U.S. PATENT DOCUMENTS

| 8,509,381 | B2 * | 8/2013 | Walker | A61B 6/08 378/39 |
| 9,192,342 | B2 * | 11/2015 | Roudergues | A61B 6/04 |
| 2005/0117693 | A1 | 6/2005 | Miyano | |
| 2006/0227939 | A1 * | 10/2006 | Walker | A61B 6/14 378/208 |

(Continued)

FOREIGN PATENT DOCUMENTS

JP     2001346796     12/2001

OTHER PUBLICATIONS

International Search Report and Written Opinion for Application No. PCT/EP2019/058909, dated May 29, 2019, 11 pages.

*Primary Examiner* — Irakli Kiknadze
(74) *Attorney, Agent, or Firm* — Michael Best & Friedrich LLP

(57) ABSTRACT

An X-ray dental imaging system for medical imaging includes a column, a housing coupled to the column, and a lower shelf movably coupled to at least one of the column or the housing.

18 Claims, 14 Drawing Sheets

(51) Int. Cl.
*A61B 6/04* (2006.01)
*A61B 6/03* (2006.01)

(58) Field of Classification Search
CPC ... A61B 6/4233; A61B 6/4405; A61B 6/4429; A61B 6/50; A61B 6/467; A61B 6/0492; A61B 6/4447; A61B 6/4482; A61B 6/461; A61B 6/527; A61B 6/541; A61B 6/548; H01L 27/1214; H01L 27/124; H01L 29/41758; H01L 29/458; H01L 29/78642; H01L 29/78669; H01L 29/78678; H04N 5/65; H04N 5/23238; H04N 5/32; G01N 23/046; G16H 50/20; G01T 1/2018; G01T 1/24; G06T 11/005; G06T 11/006; G06T 2211/408; G06T 2211/424
USPC .......................... 378/4, 19, 20, 28, 39, 208
See application file for complete search history.

(56) References Cited

U.S. PATENT DOCUMENTS

| | | |
|---|---|---|
| 2007/0183567 A1 | 8/2007 | Rotondo et al. |
| 2009/0285356 A1* | 11/2009 | Thoma ............... A61B 6/14 378/20 |
| 2010/0128840 A1 | 5/2010 | Cha |
| 2010/0278299 A1* | 11/2010 | Loustauneau ........ A61B 6/587 378/13 |
| 2011/0104634 A1 | 5/2011 | Kyöstilä |
| 2011/0141255 A1* | 6/2011 | Mori ................... A61B 6/032 348/61 |
| 2014/0079182 A1 | 3/2014 | Roudergues et al. |
| 2014/0098930 A1* | 4/2014 | Litzenberger ........ A61B 6/541 378/4 |
| 2015/0374320 A1 | 12/2015 | Suuronen et al. |
| 2017/0311915 A1 | 11/2017 | Martino et al. |
| 2019/0046279 A1* | 2/2019 | Hille ..................... B25J 9/08 |
| 2019/0059842 A1* | 2/2019 | Sugihara ............. A61B 6/5282 |

* cited by examiner

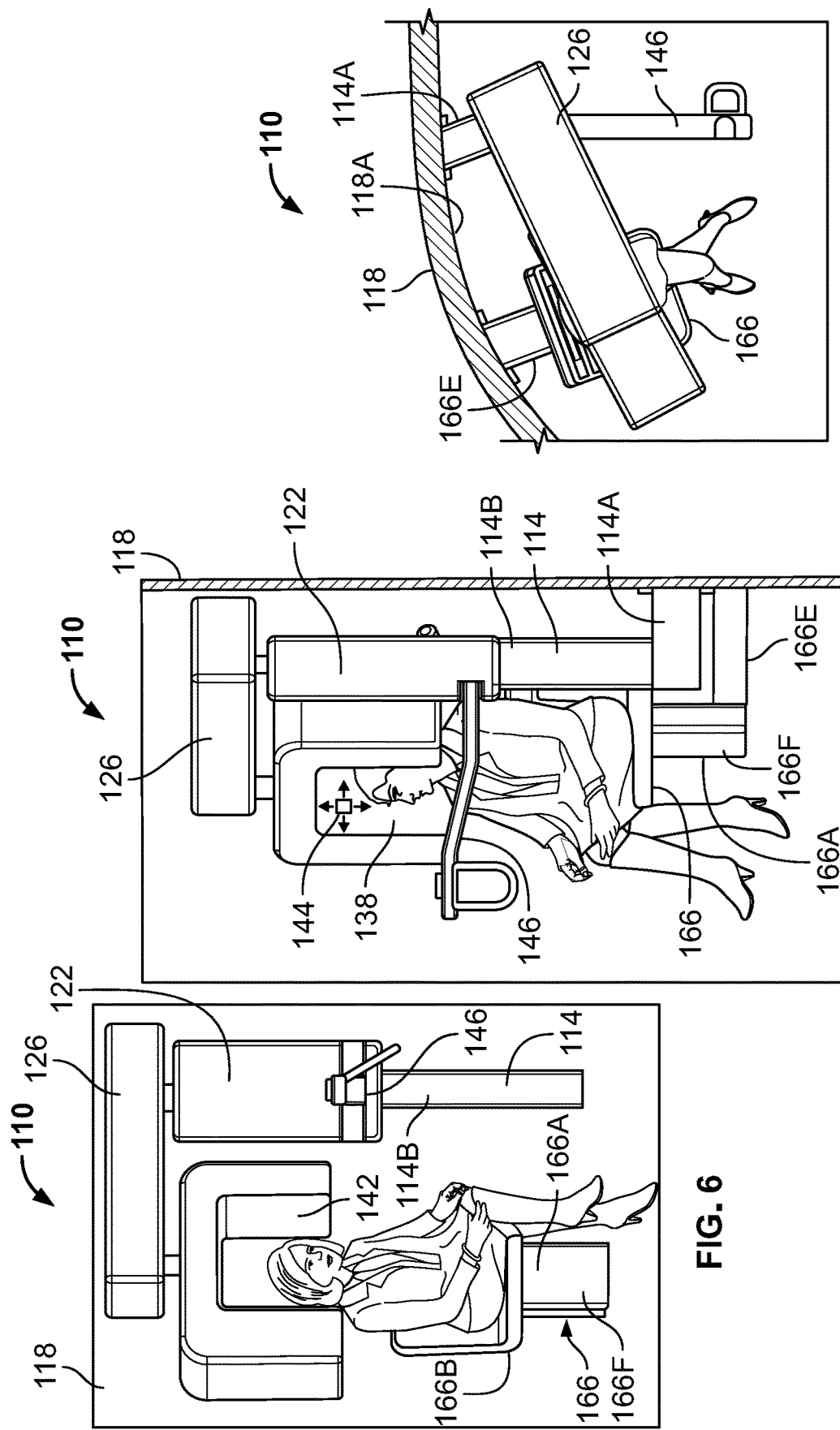

ADJUSTABLE LOWER SHELF ON AN X-RAY UNIT

FIELD OF THE INVENTION

Embodiments relate to X-ray imaging systems, and more particularly to medical X-ray imaging systems.

SUMMARY OF THE INVENTION

X-ray imaging in medical (for example dental) fields requires that a patient be positioned with respect to an X-ray imaging device so that an image of an anatomical feature or anatomy of interest may be obtained. Improper positioning of a patient may result in an image that fails to include the anatomy of interest. Patient movement may also cause this problem. Patient movement may also cause artifacts. In some instances, it is preferred that a patient stand, for example, when an image of the patient's skull or teeth is desired. However, in some instances, some patients may prefer to sit during an imaging procedure, and/or operators may prefer that the patients sit during the imaging procedure. For example, the longer an imaging takes, the easier it is to keep a patient still when he or she is sitting. Thus, operators may prefer that patients be seated during certain imaging procedures. In other instances, patients may be incapable of standing, for example, patients who have neurological disorders or injuries. Embodiments provide, among other things, an imaging system that accommodates both standing and sitting patients.

In one aspect, embodiments provide an X-ray dental imaging system for medical imaging. The X-ray imaging system includes a column, an upper shelf rotatably coupled to the column, a rotating part rotatably coupled to the upper shelf, and a chair spaced from the column.

In another aspect, embodiments provide an X-ray dental imaging system for medical imaging. The X-ray imaging system includes a column, a housing coupled to the column, and a lower shelf movably coupled to at least one of the column or the housing.

Other features and aspects of will become apparent by consideration of the following detailed description and accompanying drawings.

BRIEF DESCRIPTION OF THE DRAWINGS

FIG. 6 is a front view of an X-ray dental imaging system according to another embodiment.

FIG. 7 is a side view of the X-ray dental imaging system of FIG. 6.

FIG. 8 is a top view of the X-ray dental imaging system of FIG. 6.

Before any embodiments are explained in detail, it is to be understood that they are not limited in their application to the details of construction and the arrangement of components set forth in the following description or illustrated in the following drawings. Other embodiments are possible and are capable of being practiced or of being carried out in various ways. Also, it is to be understood that the phraseology and terminology used herein is for the purpose of description and should not be regarded as limiting.

DETAILED DESCRIPTION

Figure 1:
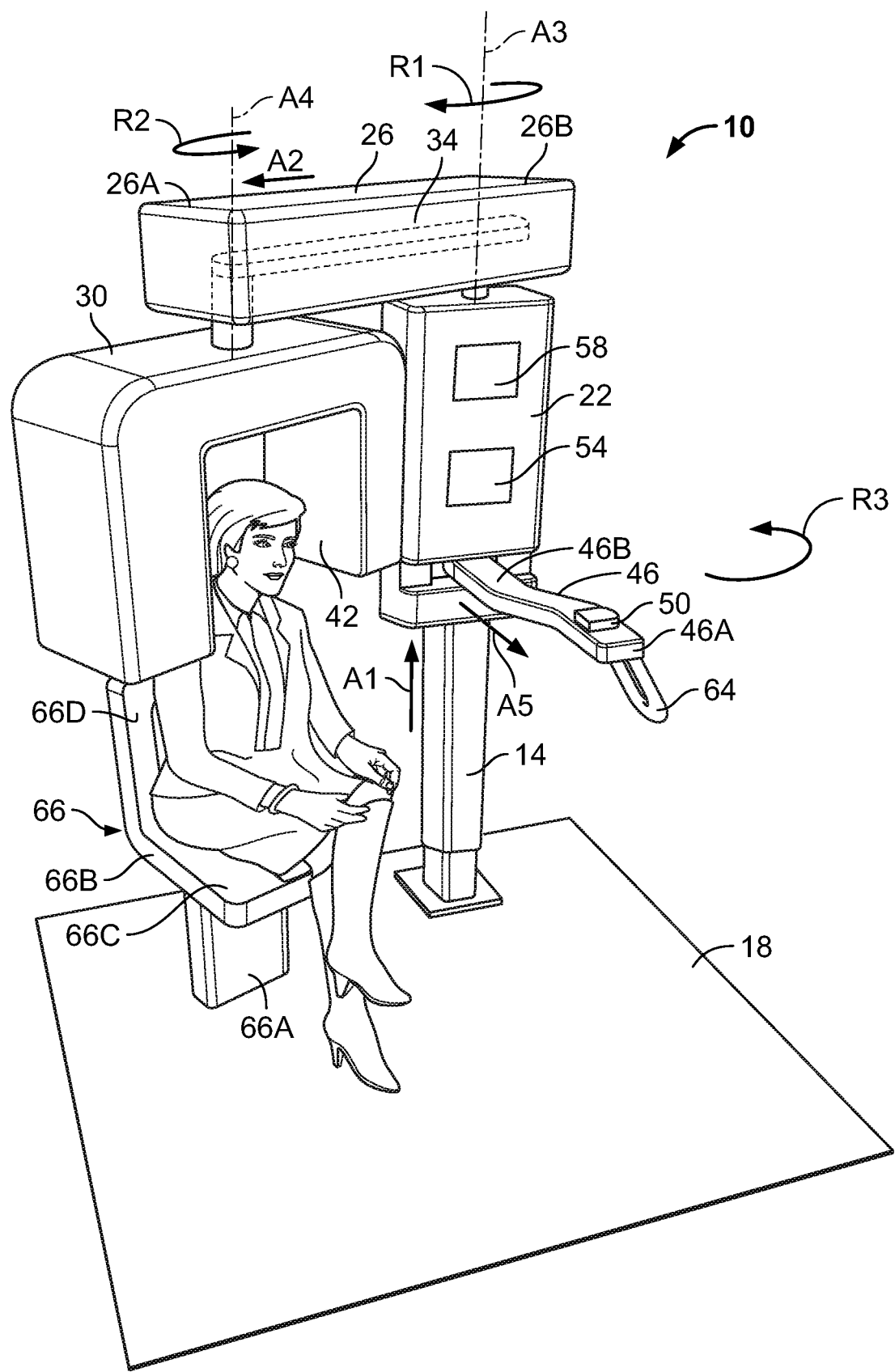
FIG. 1 is a perspective view of an X-ray dental imaging system according to one embodiment, with a seated patient.
Figure 2:
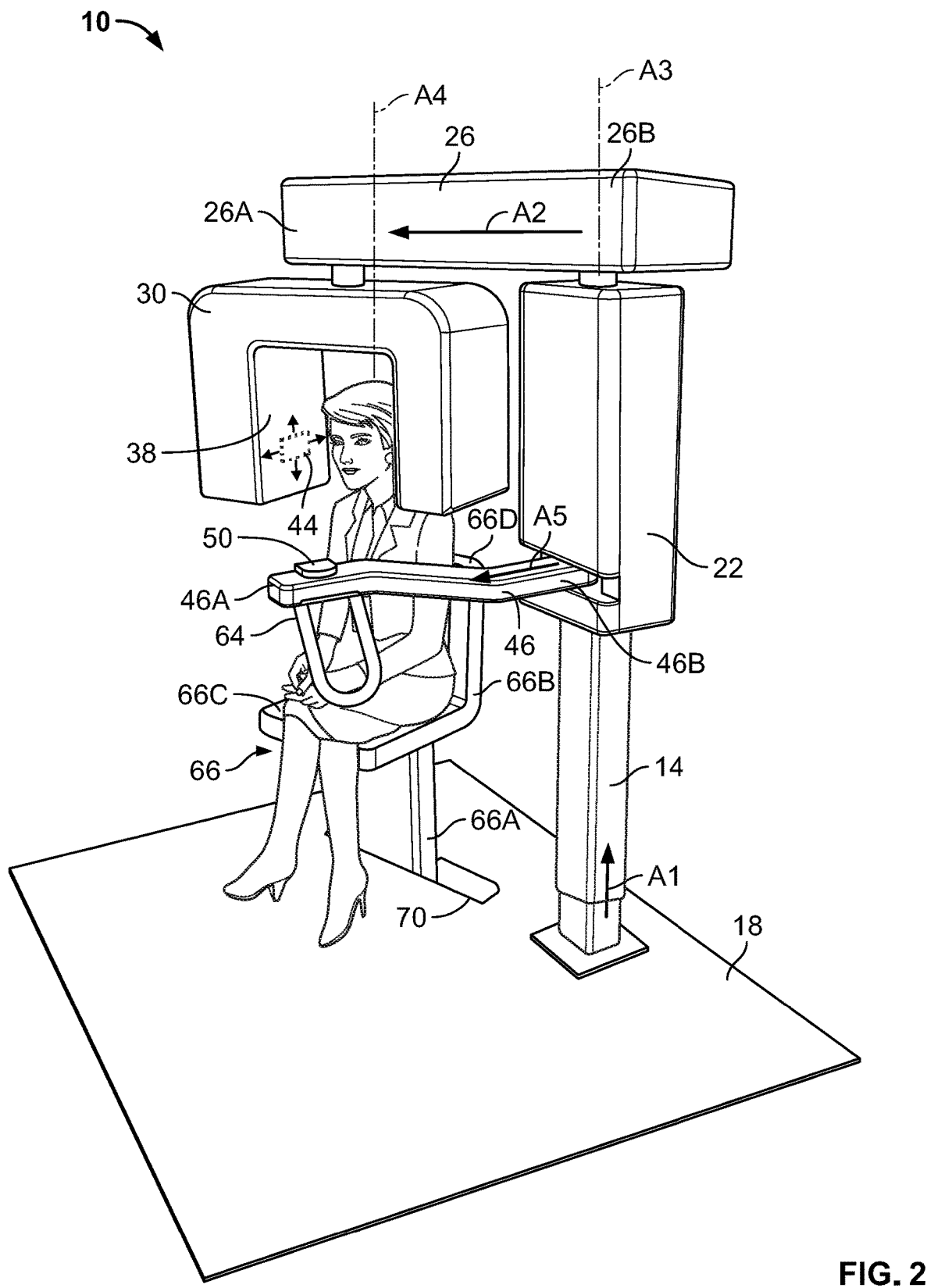
FIG. 2 is a secondary perspective view of the X-ray dental imaging system of FIG. 1.

An X-ray dental imaging system 10 is shown in FIGS. 1 and 2. The imaging system 10 includes a column 14 coupled (for example, rigidly fixed) to a frame 18. The frame 18 may be positioned at a variety of locations within a room, for example on or fixed to a floor panel, integrated as part of a floor panel, positioned on or fixed to a wall (for example, without contacting a floor panel), or integrated as part of a wall. The frame 18 may take a variety of different forms and shapes. For example, the frame 18 may have a generally flat configuration to rest on a floor panel, may have a generally elongate vertical configuration, may be round, square, or another shape, and/or be formed integrally with a lower portion of the column 14. The frame 18 may support the overall X-ray imaging system 10. In the embodiment in FIGS. 1 and 2, the column 14 extends vertically upward from and transverse to the frame 18 in a lengthwise direction, as denoted by arrow A1. The column 14 may instead extend in different directions from the frame 18 than that illustrated. The column 14 may be extendable via a telescoping arrangement (for example, may include two or more elements that telescope vertically relative to one another) to extend in the lengthwise direction A1, and to retract along a direction opposite to the direction A1 to vary an overall height of the imaging system 10.

As illustrated in FIGS. 1 and 2, the X-ray imaging system 10 further includes a housing 22 (for example, hollow box or enclosure) that is coupled (for example, mounted) to the column 14. The column 14 may extend through the housing 22. The housing 22 may slide vertically up and down relative to the column 14, or may be fixed (for example, mounted) to an upper end of the column 14 and move with the extending and retracting column 14. The housing 22 may contain or house various electrical components, as described in greater detail below.

With continued reference to FIGS. 1 and 2, the X-ray imaging system further includes an upper shelf 26 (for example, arm or top support member) that is coupled to the column 14 and/or to the housing 22 generally at an upper end of the housing 22. The upper shelf 26 is oriented along a lengthwise direction, as indicated by arrow A2, transverse to the lengthwise direction A1 of the column 14, and has a length along the lengthwise direction A2 beyond the housing 22 in at least one direction to create an overhang at a distal end 26A. A proximal end 26B of the upper shelf 26 (opposite the distal end 26A) is rotatably coupled to the column 14 about a first axis A3 such that the upper shelf 26 is rotatable around the column 14 about the first axis A3 in a first rotational direction R1 (and/or a direction opposite to the first rotational direction R1). For example, the upper shelf 26 may rotate up to 400 degrees (or other values and ranges) about the first axis A3 between a first a first position about an object to a second position about the object. A motor may be located in the upper shelf 26 or in the column 14 to rotate the upper shelf 26. The upper shelf 26 may also be translated (for example via a motor) vertically relative to the column 14 at the proximal end 26B (for example, sliding vertically along a track, via a screw shaft, etc.).

With continued reference to FIGS. 1 and 2, a rotating part 30 (for example, arm or gantry arm) is coupled to the upper shelf 26. As illustrated in FIGS. 1 and 2, the rotating part 30 may be a C-shaped gantry arm sized to fit and rotate around an object, for example a patient's head. The rotating part 30 may instead be U-shaped, or have other shapes and sizes than that illustrated. The rotating part 30 is rotatably mounted to the upper shelf 26 about a second axis A4, spaced apart from and parallel to the first axis A3. The rotating part 30 rotates in a second rotational direction R2 (and/or a direction opposite to the second rotational direction R2). For example, the rotating part 30 may rotate up to 400 degrees (or other values and ranges) about the second axis A4. The rotating part 30 is capable of rotating entirely about an object, for example a patient's head. The rotating part 30 and/or the upper shelf 26 includes one or more actuators, for example a motor-driven track or rail system 34 to provide linear movement (for example along direction A2) of the rotating part 30 relative to the upper shelf 26. The rotating part 30 supports an X-ray source 38 (FIG. 2) at one end of the C-shaped arm and a detector unit 42 (FIG. 1) at an opposite end. The X-ray source 38 generates an X-ray beam, and the detector unit 42 detects the X-ray beam. The X-ray source 38 and the detector unit 42 are positioned opposite one another such that a head of a patient (for example, child or adult) can be positioned therebetween to produce (for example, provide data for), for example, a panoramic, computed tomography, or cephalometric image. As illustrated in FIG. 2, a beam limiting device 44 may be affixed to the X-ray source 38 to control a width and height of the X-ray beam emitted from the X-ray source 38. The beam limiting device 44 may be adjusted (for example, with a motor) in various directions, as illustrated by the arrows in FIG. 2.

The X-ray source 38 may be common for at least two imaging modes (for example, panoramic and computed tomography). The detector unit 42 may include one or more X-ray detectors that may be positioned and movable relative to one another depending on the type of image being taken. For example, U.S. Patent Publication No. 2015/0374320, the entire contents of which are incorporated by reference herein, describes examples of X-ray detectors 227a, 227b that are used for various types of imaging, as well as how the detectors are positioned based on the types of images being taken. Additionally, the detector unit 42 overall (or one or more of the X-ray detectors therein) may be adjustable, for example by rotating the detector unit 42 relative to a remaining portion of the rotating part 30 or by translating the detector unit 42 linearly relative to a remainder of the rotating part 30). A motor or motors may be provided to permit the adjustable movement of the detector unit 42 and/or its X-ray detector(s).

With reference to FIGS. 1 and 2, a lower shelf 46 (for example, arm) is coupled to the housing 22. The lower shelf 46 may be rotatably coupled to the housing 22. For example, as illustrated in FIG. 1, the lower shelf 46 may rotate (for example, pivot) horizontally relative to the housing 22 in a third rotational direction R3 (and/or a direction opposite to the third rotational direction R3), generally about a vertical axis that is parallel to the direction A1.

The lower shelf 46 may be a frame member that includes an arm that extends from a proximal end 46B at the column 14 to a distal end 46A. The lower shelf 46 may extend generally in a lengthwise direction, as indicated by arrow A5 in FIGS. 1 and 2, transverse to the lengthwise direction A1 of the column 14. The lower shelf 46 may be rotatable relative to the housing 22 and translate along the length of the column 14 (for example, vertically up and down) with the housing 22. The lower shelf 46 may accommodate a patient at various heights and positions, for example for a standing patient and a seated patient.

Figure 3:
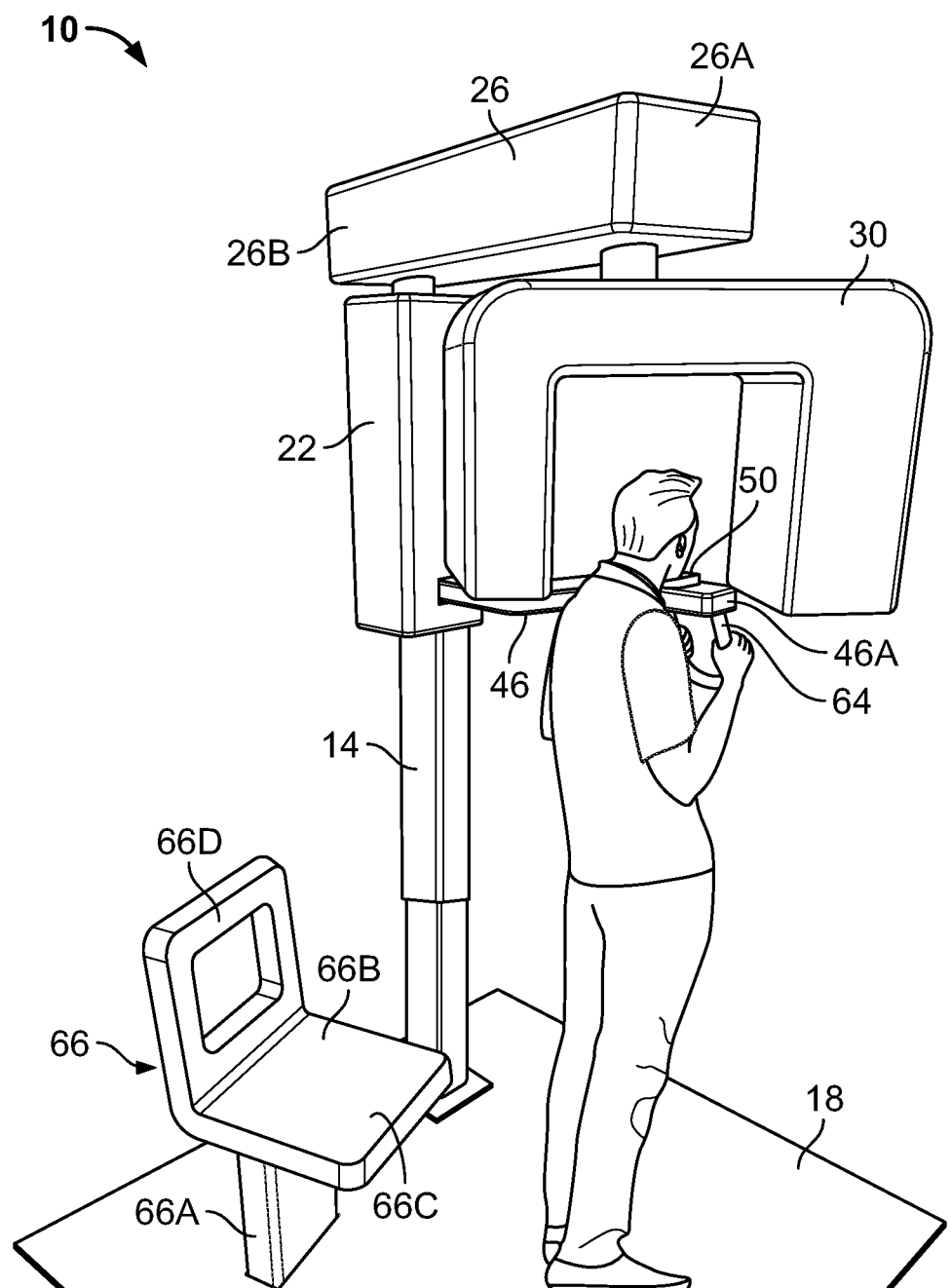
FIG. 3 is a perspective view of the X-ray dental imaging system of FIG. 1 with a standing patient.
Figure 4:
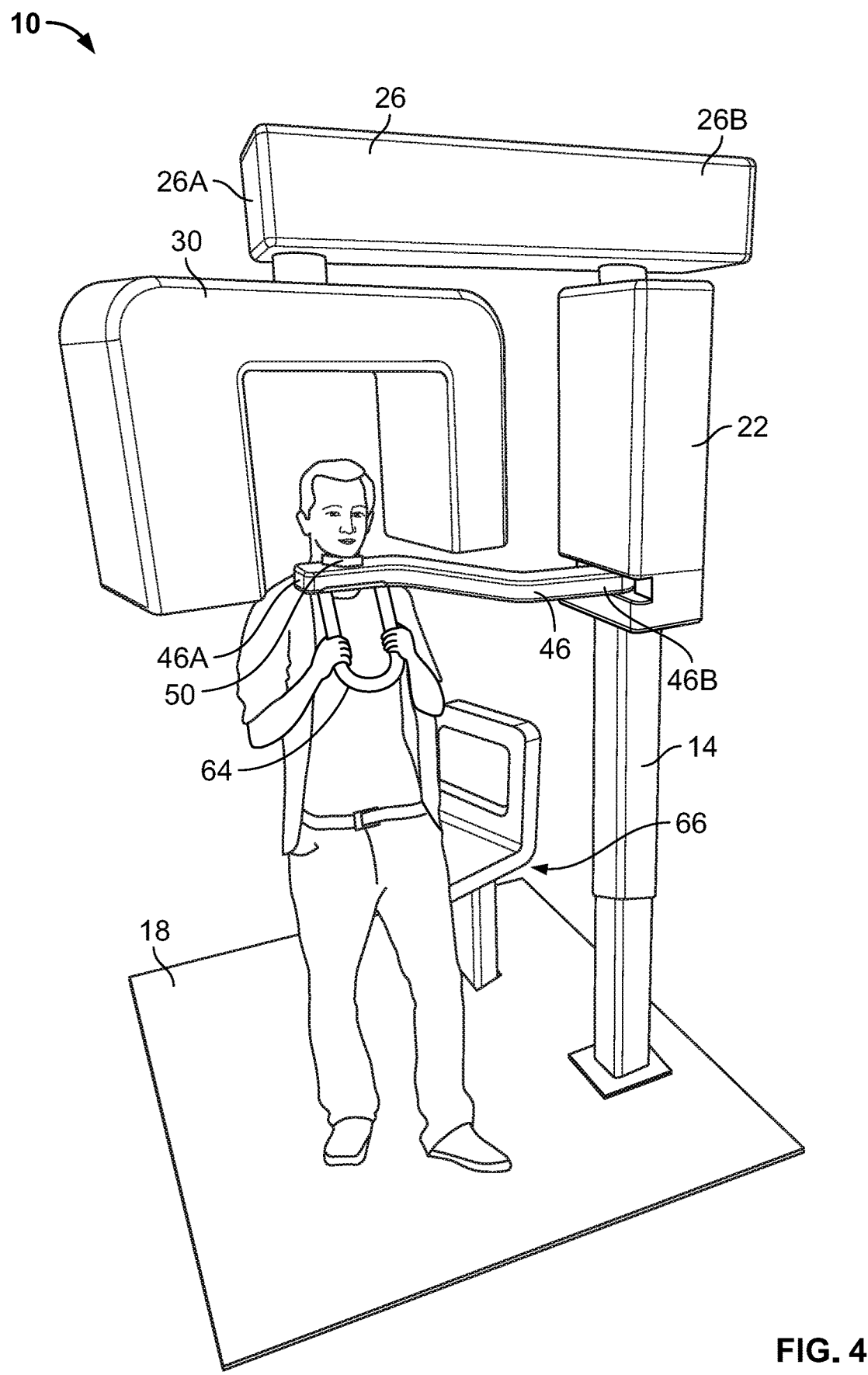
FIG. 4 is a secondary perspective view of the X-ray dental imaging system of FIG. 3.
Figure 5:
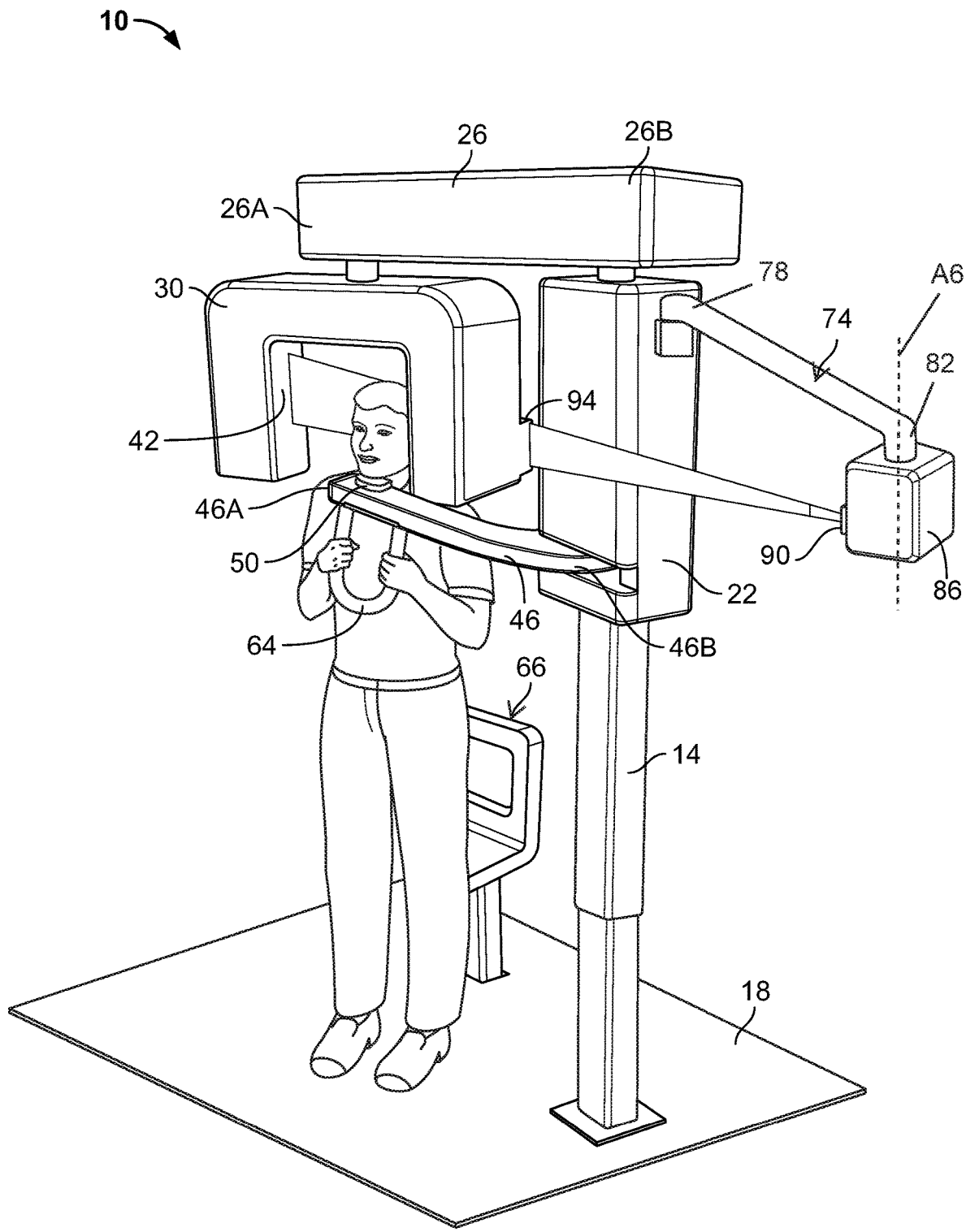
FIG. 5 is a perspective view of the X-ray dental imaging system of FIG. 3, with an added cephalometric arm.

With reference to FIGS. 3-5, the lower shelf 46 may include a head support 50 (for example, support frame) that is coupled to the distal end 46A of the lower shelf 46. The head support 50 may be a non-planar frame structure that includes a chin block contoured to support a chin of a patient. The lower shelf 46 may be non-linear, having a jog between the distal end 46A and the proximal end 46B, although the lower shelf 46 may instead extend entirely linearly between the distal end 46A and the proximal end 46B, or may have shapes and sizes other than that illustrated (for example a more arcuate shape such as that illustrated in FIG. 5). As illustrated in FIGS. 1-5, a handle 64 may be coupled to the lower shelf 46. The handle 64 provides, for example, a handhold for a user (i.e., the operator, the patient) to manually rotate the lower shelf 46 relative to the housing 22. If the lower shelf 46 is locked in a specific position, the handle 64 provides a handhold for a patient to balance relative to the lower shelf 46. In other embodiments the handle 64 is not provided, or has a different shape or size than that illustrated. In some embodiments the lower shelf 46 and head support 50 may be arranged such that the patient faces the column 14. In some embodiments the lower shelf 46 may be movable (for example vertically and/or horizontally) relative to the column 14 without being fixed to the column 14 at any end or having a portion that extends into the column 14.

While FIGS. 1-5 illustrate a lower shelf 46 that is rotatably coupled to the housing 22, the lower shelf 46 alternatively may be rotatably coupled directly to the column 14. For example, the column 14 may be cylindrical (i.e., having a circular cross-section) and the lower shelf 46 may include a collar or other structure that extends around the column 14, allowing the lower shelf 46 to rotate (for example, swing) directly around the column 14.

Similar to the upper shelf 26, the lower shelf 46 may be automatically rotated by a motor (not shown) or may otherwise be manually rotated. The housing 22, column 14, and/or the lower shelf 46 may be provided with one or more bearing surfaces to enable the rotational movement of the lower shelf 46. Further, the lower shelf 46 may be lockable at various rotational positions, either by a physical locking interface (for example, a pin and aperture arrangement), a detent structure, by friction within a drivetrain (for example, if the lower shelf 46 is rotatable via a motor), or via other mechanisms.

With continued reference to FIGS. 1-5, the X-ray imaging system 10 includes a chair 66. The chair 66 may be spaced apart from the column 14 by a distance (for example, a fixed distance, or a variable distance). The chair 66 may include, for example, a stem 66A coupled to (for example, rigidly fixed to or formed integrally as part of) the frame 18, and a seat 66B coupled to the stem 66A to provide a seat surface for the patient. As illustrated in FIGS. 1 and 2, the seat 66B includes a lower first surface 66C for supporting the upper legs of the patient and an upper second surface 66D for supporting the lower back of the patient. The stem 66A may be adjustable relative to the frame 18 to adjust a height of (for example, raise and lower) the first surface 66C to accommodate varying patient heights. Further, at least a portion of the chair 66 may be rotationally adjustable relative to the frame 18 (for example rotatable about an axis extending parallel to the direction A1). The chair 66 may rotate for example 90°, 180°, or various other angles and ranges to accommodate for different X-ray imaging. Additionally, the chair 66 may be lockable at various heights and rotational angles to prevent unwanted rotation when the X-ray source 38 is in use. While shown as an upright seated chair 66, at least a portion of the chair 66 (for example the seat 66B) may otherwise be relaxed and tilted back (for example via adjustment by the patient or operator) at an angle to provide an appropriate angle for conducting an X-ray image. Other embodiments include various other chairs 66, including chairs with cushioning, padding, back and leg supports, etc.

As shown in FIG. 2, the chair 66 may translate relative to the frame 18. For example, the chair 66 may move along a rail 70 positioned on or in the frame 18. Translation along the rail 70 moves the seat 66B of the chair 66 nearer or farther from the column 14. Therefore, the rotating part 30 can be positioned about the head of the patient by either translating the chair 66 relative to the frame 18, by translating the rotating part 30 relative to the upper shelf 26, or by a combination of the two.

With reference to FIG. 1, the system 10 may include or house a controller 54 (for example, a microprocessor, memory, and related components). The controller 54 is programmed to control various aspects of the X-ray imaging system 10. For example, the controller 54 can be programmed to receive operator input via an input device 278 (FIG. 9), produce an output via the X-ray source 38, cause motors or similar devices to rotate the upper and/or lower shelves 26, 46 about the first rotational axis A3, and rotate the rotating part 30 about the second rotational axis A4. The controller 54 can signal a motor 58 to rotate the upper shelf 26 until the rotating part 30 is positioned around the head of the patient. If the patient is seated, the controller 54 can use inputs (for example, from sensors) to determine a distance between the chair 66 and the column 14 to approximate or determine the desired position of the rotating part 30. The controller 54 can also actuate the motor 58 to translate the rotating part 30 along the upper shelf 26, translate the upper shelf 26 and/or housing 22 along the column 14 and/or rotate the lower shelf 46 relative to the housing 22.

With reference to FIG. 5, the X-ray imaging system 10 may include a cephalometric arm 74 having a proximal end 78 coupled to the housing 22 or the column 14 (for example, rotatably coupled or fixed to the housing 22 or the column 14). The cephalometric arm 74 includes a distal end 82 having a second X-ray source 86 to be used in cephalometric imaging, and a second beam limiting device 90 coupled to the second X-ray source 86. As illustrated in FIG. 5, the rotating part 30 may include a collimator 94 (for example, positioned to the side of the first X-ray source 38). The second X-ray source 86 may be rotated about a third axis A6 to generate a cephalometric scan. The third axis A6 may be a vertical axis that is parallel to the first and second axes A3 and A4. The second beam limiting device 90 may additionally or alternatively be moved (for example, translated linearly, similarly to the beam limiting device 44 in FIG. 2) relative to the second X-ray source 86 to facilitate a scan. As illustrated in FIG. 5, during a cephalometric imaging, the cephalometric arm 74 has been rotated or otherwise moved into a position such that the second X-ray source 86 may emit an X-ray beam toward the detector unit 42 of the rotating part 30. U.S. Patent Publication No. 2015/0374320, the entire contents of which are incorporated herein by reference, discloses further examples of cephalometric arms 160, 260, 261 that may be coupled to the column 14 and used with the imaging system 10 (see for example paragraphs [0011], [0079], [0082] and FIGS. 1a-b and 2a-d). In some embodiments the cephalometric imaging will have a third patient positioning location, requiring a second cephalometric arm such as arm 260 in U.S. Patent Publication No. 2015/0374320.

With reference to FIGS. 1 and 2, the X-ray imaging system 10 can be used when the patient is in a seated position. When in the seated position upon the chair 66, an operator (for example, technician) or the controller 54 can adjust the height of the chair 66 and spacing of the chair 66 relative to the column 14. These adjustments may be made prior to the patient sitting on the chair 66. Once the position of the chair 66 is set, the upper and lower shelves 26, 46 and the rotating part 30 may be automatically rotated and translated to fit around the desired object (for example, around the patient's head) based on the spatial relationship between the chair 66 and the column 14. Alternatively, an operator may manually adjust the position of the upper and lower shelves 26, 46 and the rotating part 30. This manual adjustment may include physically rotating and translating the various components and/or providing an input to an electromechanical system including the controller 54 and the motor(s) (including motor 58). Once the head of the patient is properly positioned within the rotating part 30, the operator can actuate the X-ray source 38 to generate the X-ray. The lower shelf 46 (and specifically the head support 50) may be rotated into contact with the head of the patient as a support structure to maintain the positioning of the head as an X-ray image is taken or captured.

FIGS. 3 and 4 illustrate the X-ray imaging system 10 positioned (or otherwise adjusted for use) when a patient is in a standing position. When it is desirable to have a patient stand during an imaging procedure (at a location away from the chair 66), an operator or the controller 54 adjusts the height of the imaging system 10 by adjusting (for example, telescopically) the overall height of the column 14 to adjust the height of the rotating part 30. When the rotating part 30 is at the appropriate height such that the object (for example, the patient's head) is properly aligned with the rotating part 30 and the detector unit 42, the lower shelf 46 is positioned such that the patient's chin rests upon the head support 50. Similar to when a patient is in a seated position, rotation and translation of the upper and lower shelves 26, 46 may be automatically or manually actuated into the appropriate position. Once the head of the patient is properly positioned within the rotating part 30, an operator can actuate the X-ray source 38 to generate the X-ray toward the detector unit 42. The rotating part 30 is thus adjustable to accommodate a patient, regardless if the patient is standing or sitting.

The X-ray imaging system 10 can be programmed to function in one, some, or all of a panoramic imaging mode, a computed tomography imaging mode, and a cephalometric imaging mode. The panoramic imaging mode, also known as panoramic radiography, is a dental imaging mode that captures the entire mouth in a single two-dimensional image, including the teeth, upper and lower jaws, surrounding structures and tissues. When in use in the panoramic imaging mode, the rotating part 30 moves the X-ray source 38 and detector unit 42 along a particular path that produces a flat two-dimensional image of the curved jaw structure. The computed tomography imaging mode, also known as a CT scan, makes use of X-ray measurements taken at different angles to produce cross-sectional, or tomographic, images of a specific area of the scanned object. When the X-ray imaging system 10 is in the computed tomography imaging mode, the rotating part 30 may rotate around the object (i.e., patient's head, for example 180 degrees), capturing multiple images from different angles. These images are reconstructed to create a three-dimensional image. The cephalometric imaging mode produces an X-ray image, for example a profile of the patient's head, showing not only the dental structure, but the surrounding tissue and nasal passageways. When in use in the cephalometric imaging mode, the rotating part 30 (or other cephalometric arm) is positioned relative to the object, and the X-ray is taken. In some embodiments both the rotating part 30 and the patient are stationary (for example when a detector is large enough to take one cephalometric shot). The X-ray imaging system 20 is configured such that the same imaging mode may be used regardless of whether the patient is in a standing or seated positions. Thus, the panoramic imaging mode, the computed tomography imaging mode, and/or the cephalometric imaging mode, may be used regardless of whether the patient stands or sits.

FIGS. 6-8 illustrate an alternative embodiment in the form of an X-ray imaging system 110. The embodiment shown in FIGS. 5-7 shares certain similarities with embodiments illustrated with respect to FIGS. 1-5. The same or similar elements are labeled with like reference numerals, incremented by 100. The functionality of the X-ray source 138 and detector 142 are similar to those described above with respect to FIGS. 1-5. In the imaging system 110, a wall panel frame 118 is a support wall or wall panel. The wall panel frame 118 replaces or is in addition to the frame 18 shown in FIGS. 1-5. In the example illustrated in FIG. 8, the wall panel frame 118 is a curved wall panel having an arcuate surface 118A that extends at least partially around the column 114 and the chair 166, with the column 114 extending from a first end of the wall panel frame 118 and the chair 166 extending from a second, opposite end of the wall panel frame 118. As shown in FIG. 7, the column 114 is L-shaped, including a first portion 114A mounted to the wall panel frame 118 at a height above a floor, and a second portion 114B extending upward (i.e., away from the floor) from the first portion 114A at a ninety degree angle. A housing 122, upper shelf 126, and lower shelf 146 are provided in a similar manner to the mounting arrangement of the housing 22 and shelves 26, 46 shown in FIGS. 1-5.

The chair 166 is likewise coupled (for example, mounted) to the wall panel frame 118. The stem 166A of the chair 166 is L-shaped, including a first portion 166E mounted to the wall panel frame 118 at a height above the floor, and a second portion 166F extending upward from the first portion 166E at a ninety degree angle, and terminating at the seat 166B.

Figure 9:
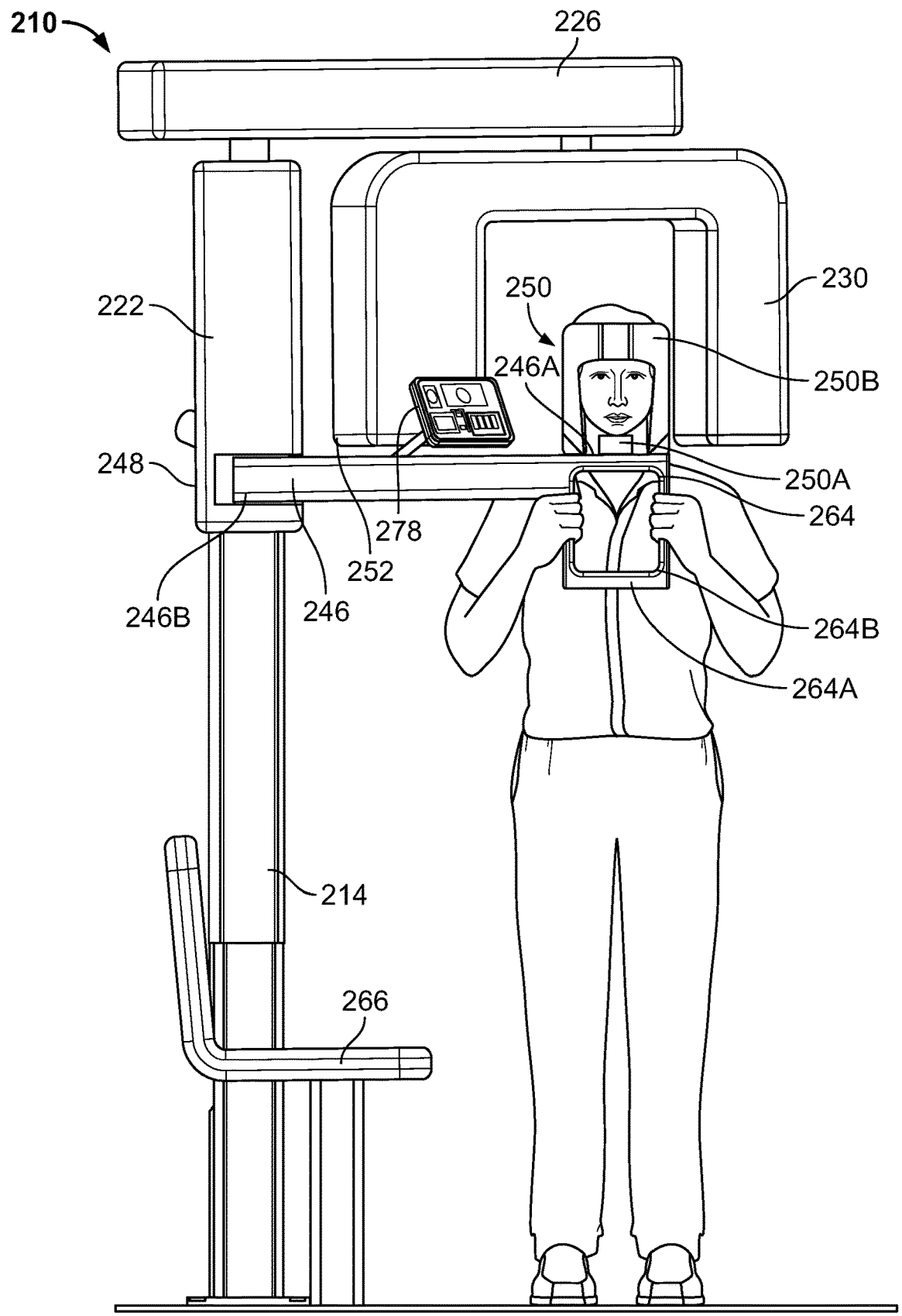
FIG. 9 is a side view of an X-ray dental imaging system according to yet another embodiment, the X-ray imaging system having a standing patient.
Figure 10:
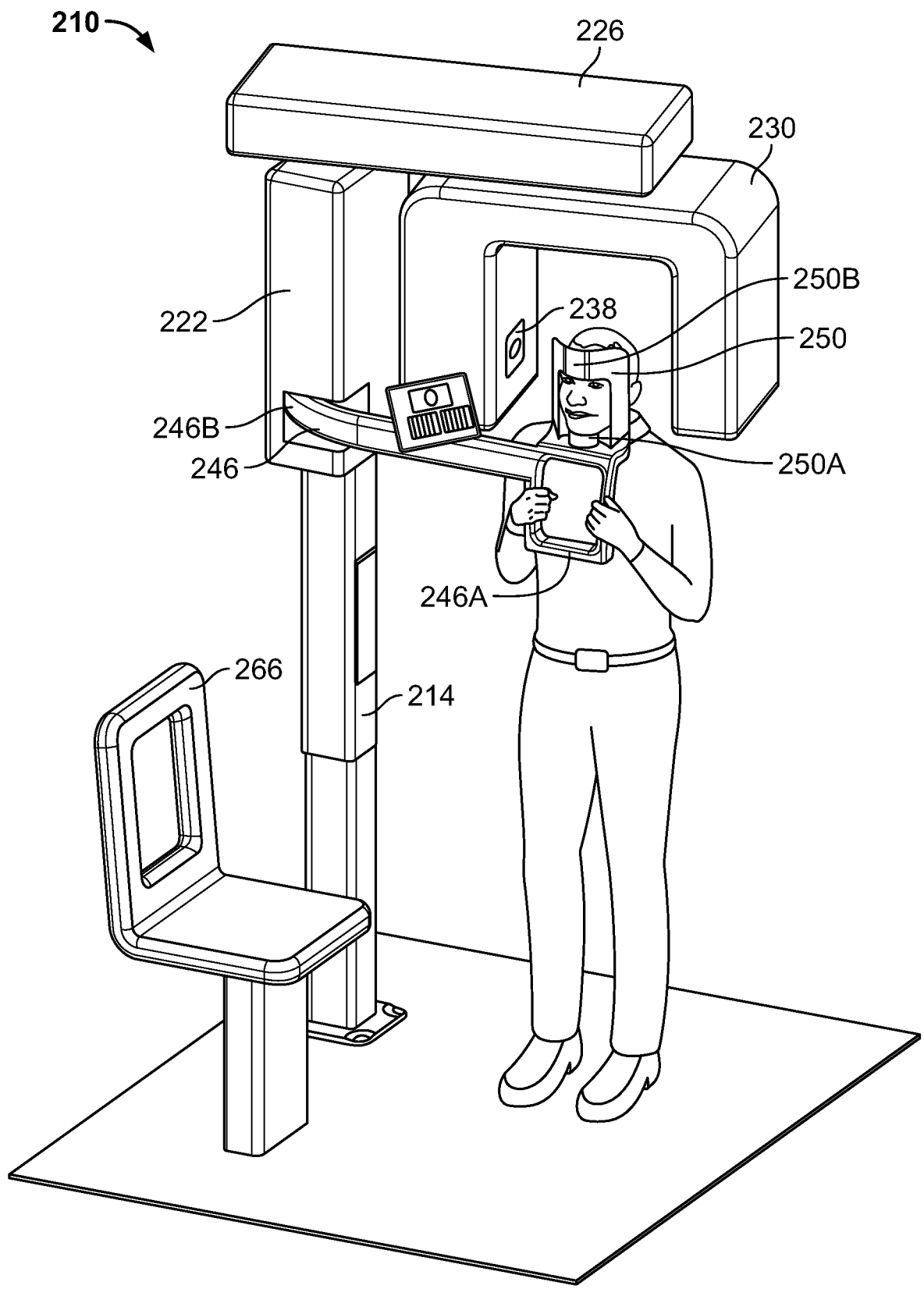
FIG. 10 is a perspective view of the X-ray dental imaging system of FIG. 9.
Figure 11:
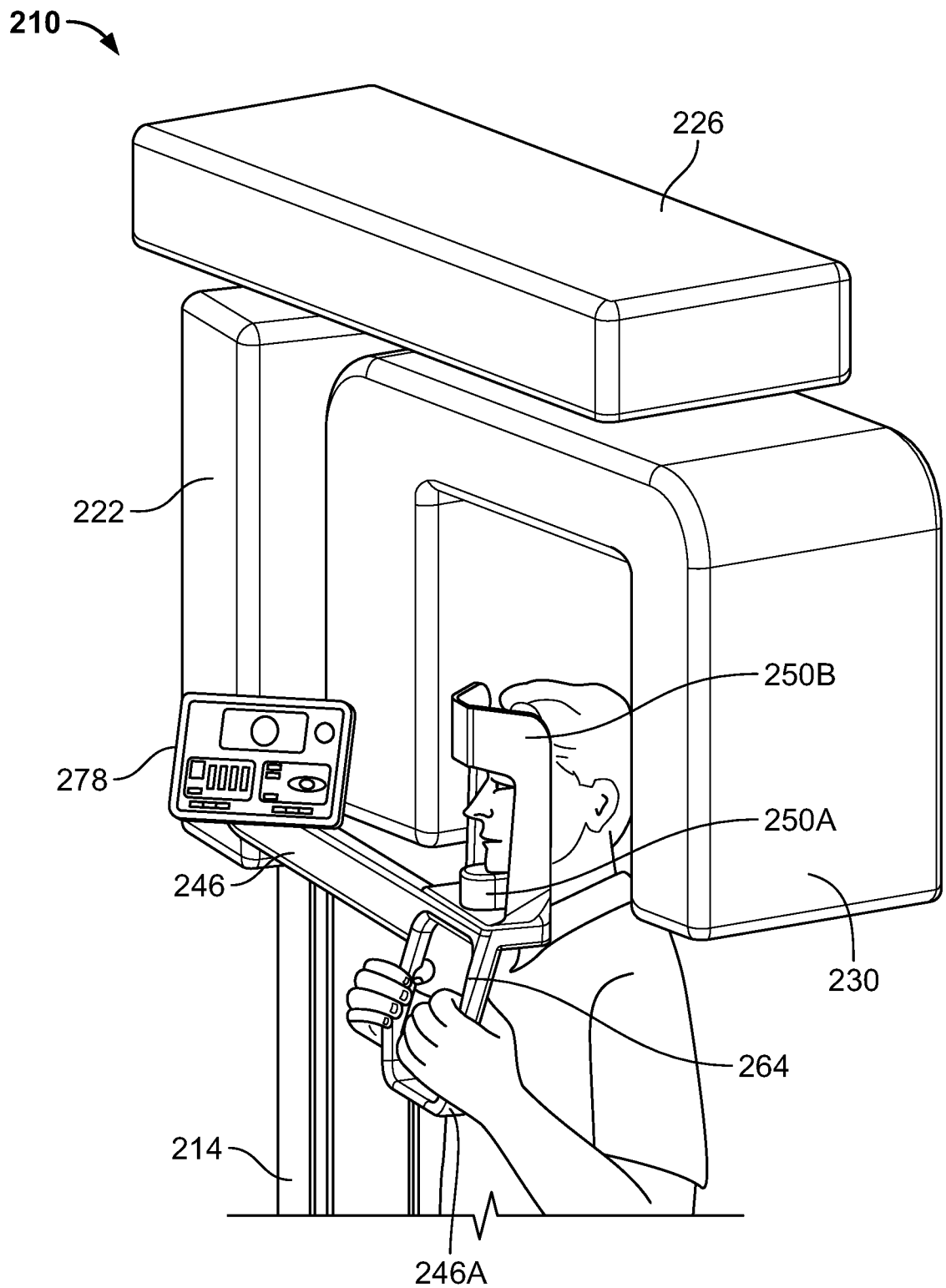
FIG. 11 is a partial perspective view of the X-ray dental imaging system of FIG. 9.
Figure 14:
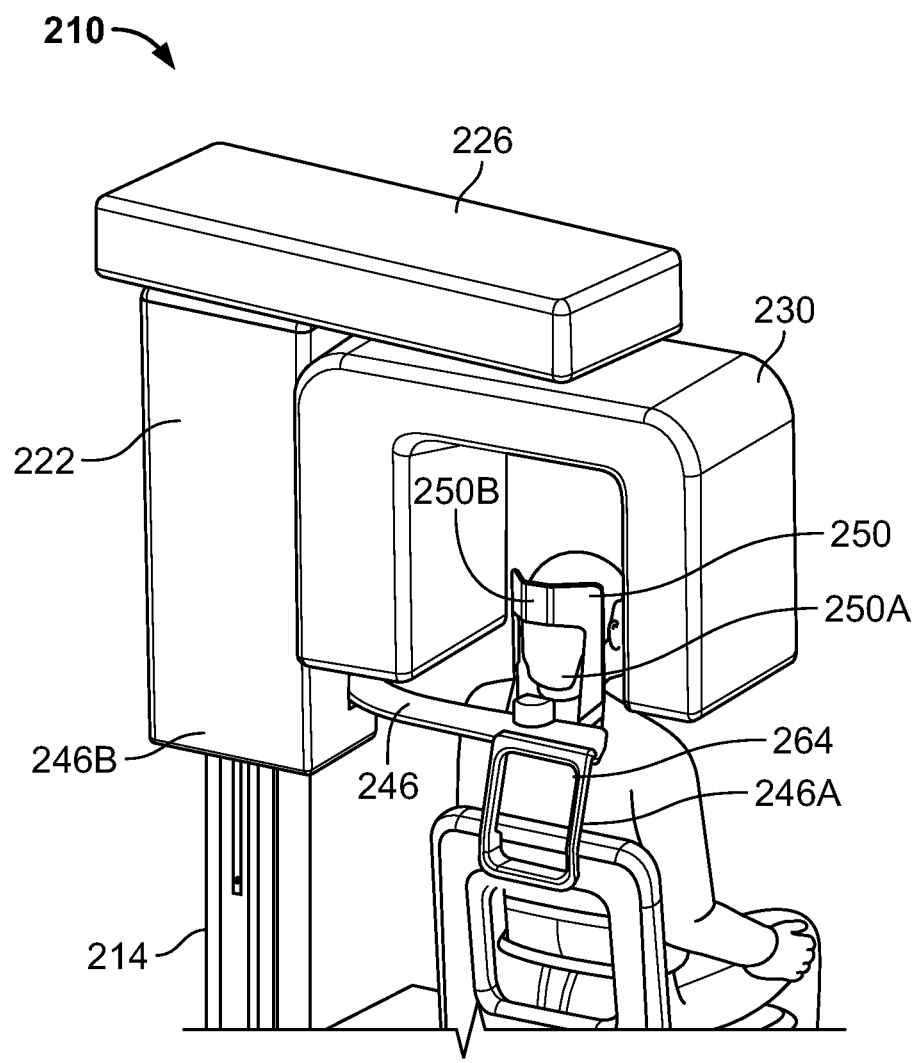
FIG. 14 is a partial rear perspective view of the X-ray dental imaging system of FIG. 12.
Figure 15:
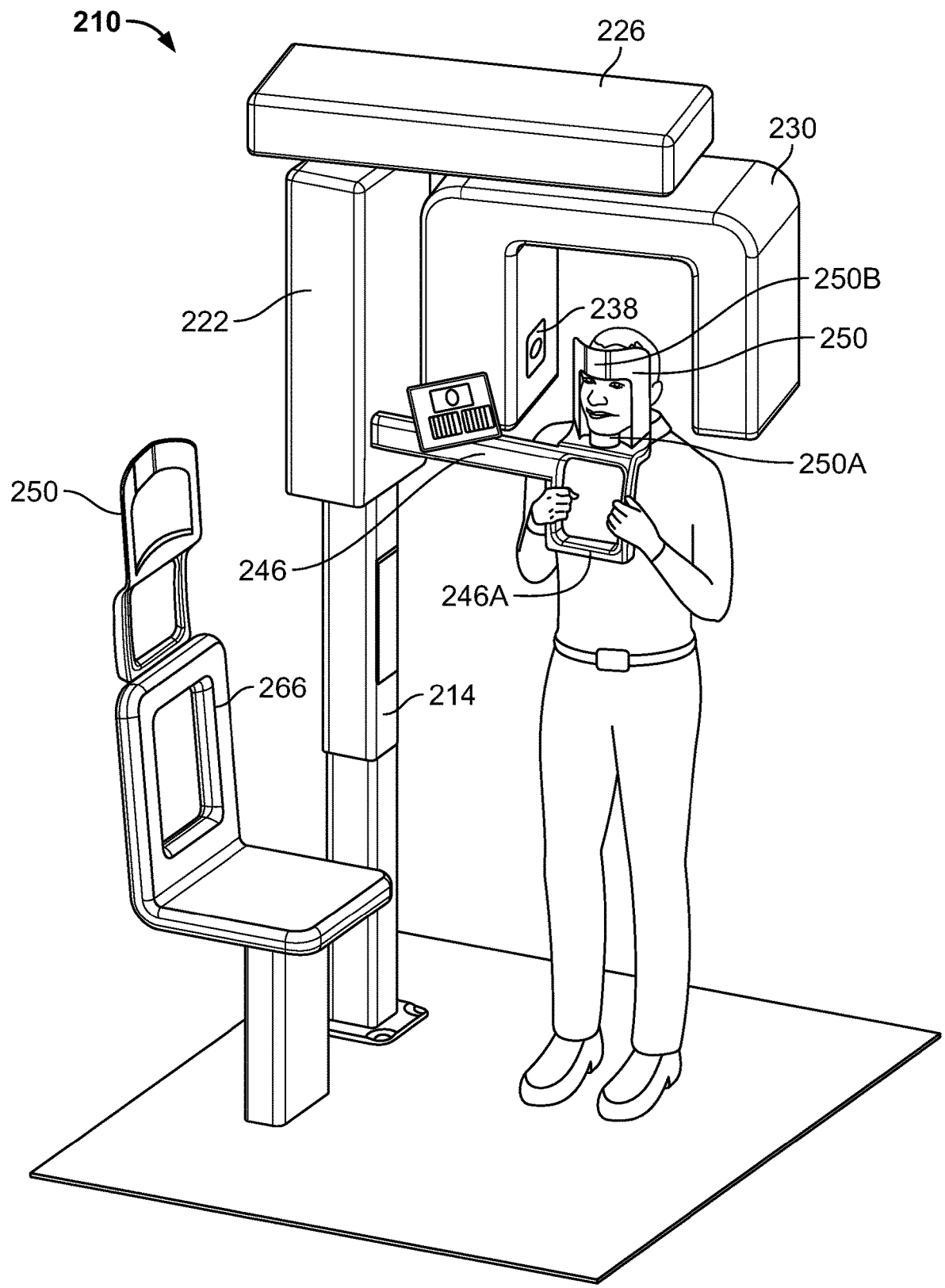
FIG. 15 is a perspective view of the X-ray dental imaging system of claim 12, illustrating a fixed lower shelf and head support.
Figure 16:
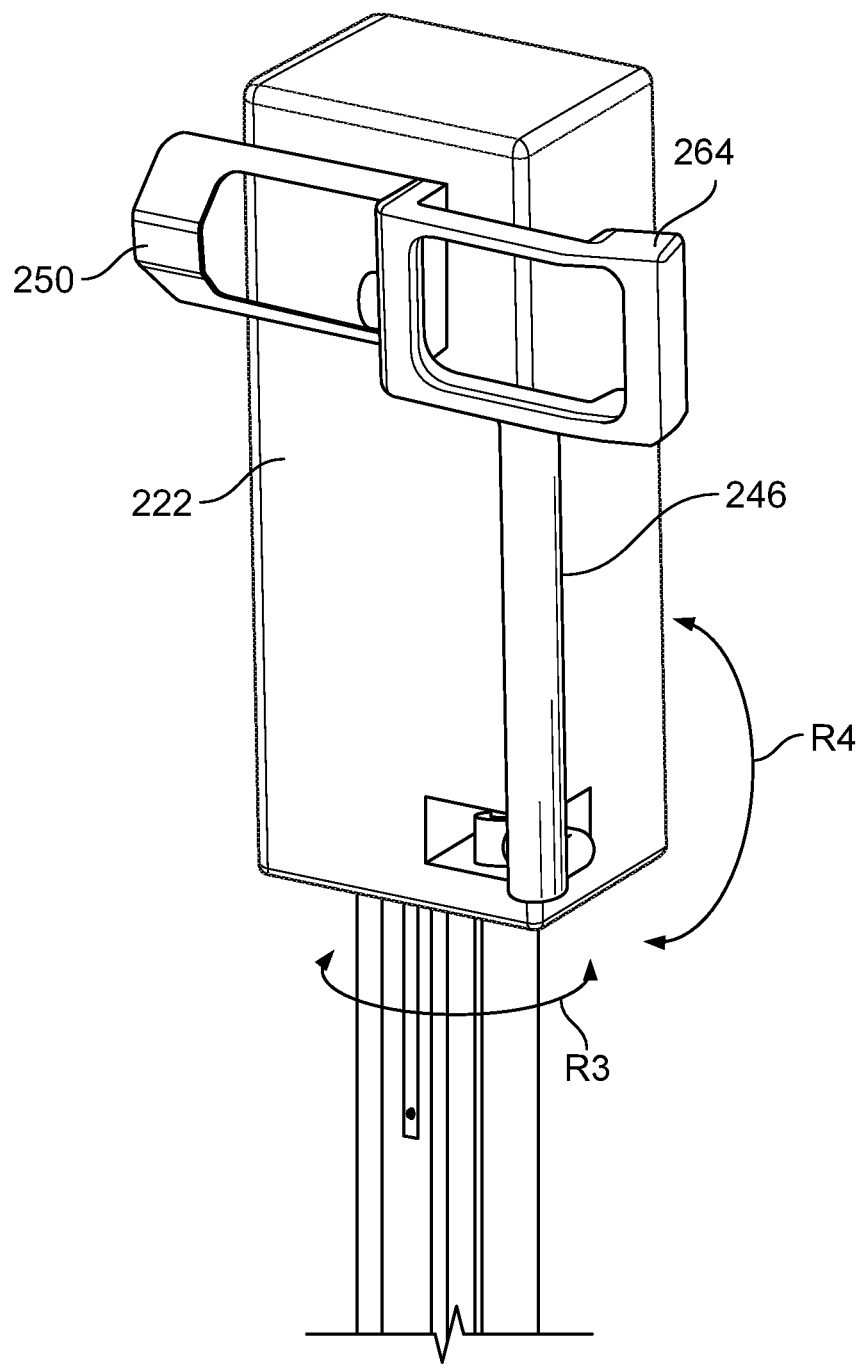
FIG. 16 is a partial perspective view of the X-ray dental imaging system of claim 12, illustrating a lower shelf that rotates both horizontally as well as vertically.

FIGS. 9-16 illustrate yet another embodiment of an X-ray imaging system, namely X-ray imaging system 210. Like elements are labeled with like reference numerals, incremented by 200 from the embodiment shown in FIGS. 1-5. As illustrated in FIGS. 9-14 and 16, the X-ray imaging system 210 includes a lower shelf 246 that can be coupled to a housing 222 (for example rotatably coupled or fixed to the housing 222). As illustrated in FIG. 9, a proximal end 246B of the lower shelf 246 extends from the housing 222 to a distal end 246A of the lower shelf 246. At the distal end 246A, the shelf 246 extends downwardly into a handle 264 and upwardly into a head support 250 (for example, a non-planar head support element). The handle 264 includes at least one vertically extending rod 264A and/or a horizontal rod 264B that function as individual handholds for the patient. The head support 250 is generally curved to correspond to a profile of the patient's head. As shown in FIGS. 9-11, the patient may place his or her chin onto a chin block 250A of the head support 250, for example, and his or her forehead against an upper portion 250B (for example, head rest) of the head support 250 to retain the head position of the patient when in the standing position. Other embodiments include various other configurations for the handle 264 and/or the head support 250. For example, as illustrated in FIG. 16, in some embodiments a portion of the handle 264 may extend both above and below the distal end of the lower shelf 246.

Figure 12:
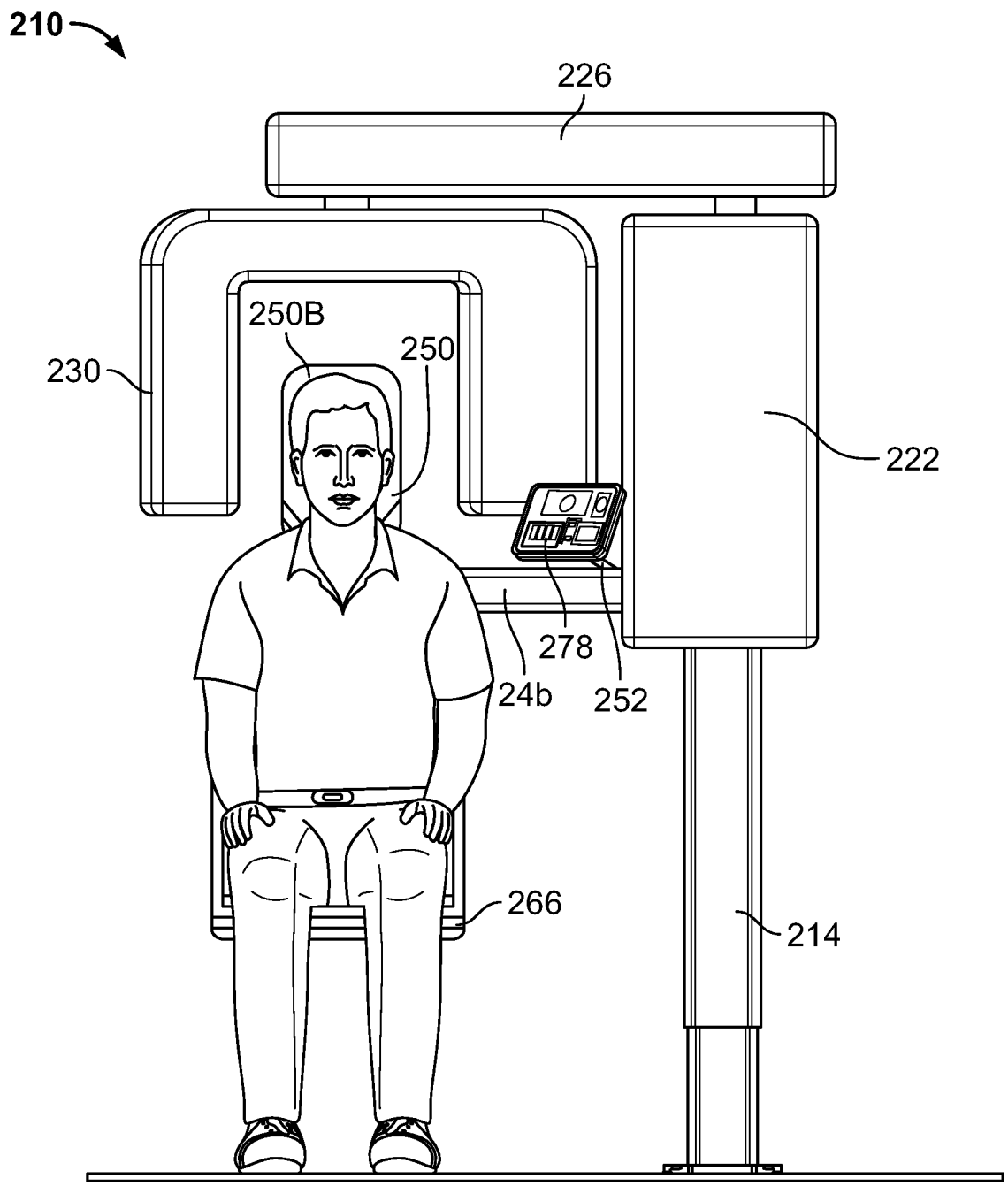
FIG. 12 is a front view of the X-ray dental imaging system of FIG. 9, the X-ray dental imaging system having a seated patient.
Figure 13:
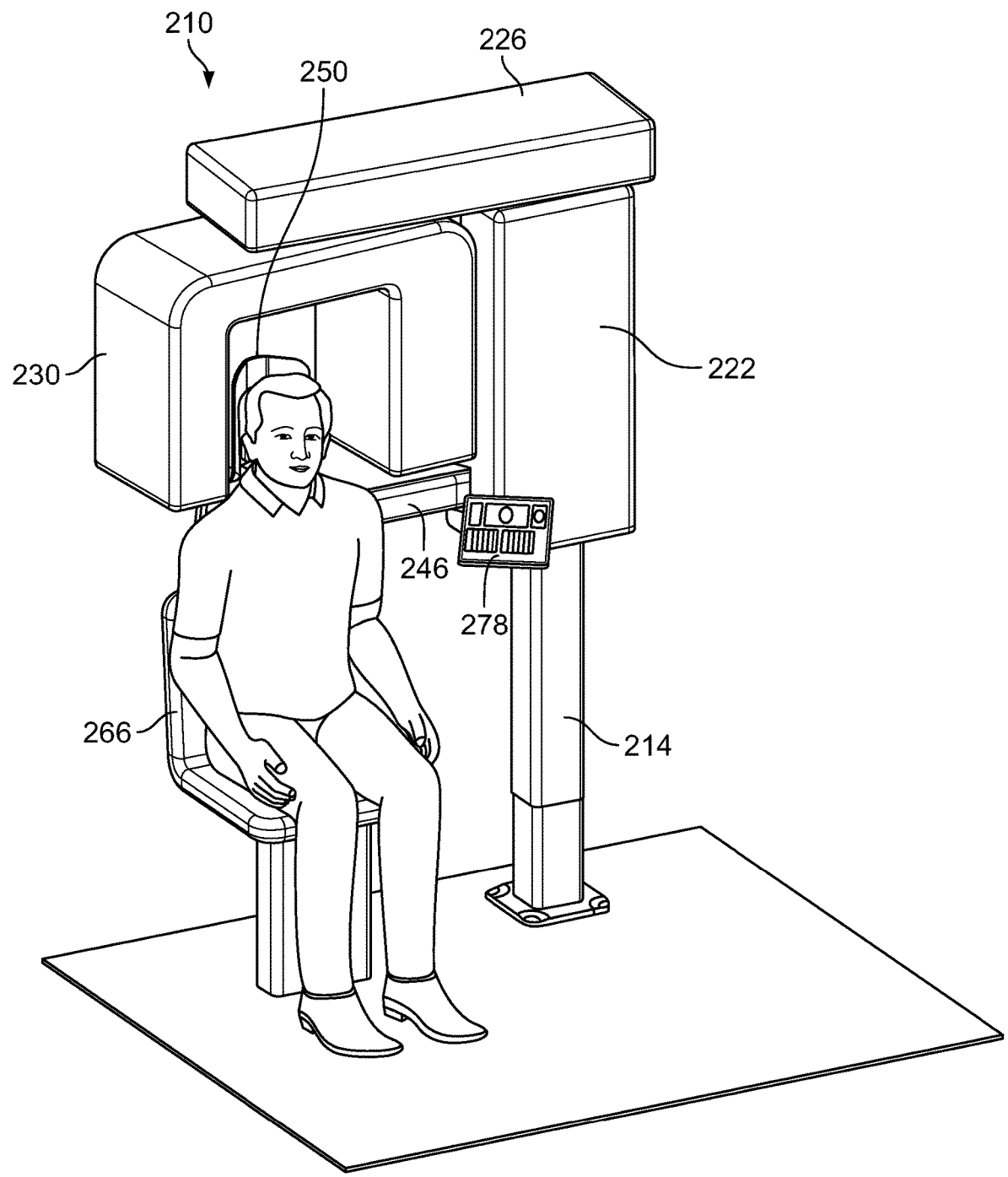
FIG. 13 is a perspective view of the X-ray dental imaging system of FIG. 12.

With reference to FIGS. 12-14, the lower shelf 246 can be rotated around to the rear of a seated patient in the chair 266. The head support 250 functions in this seated position as a rear head support, as the rear of the head of the patient (for example, the parietal bone or the occipital bone) is rested against the upper portion 250B of the head support 250 to retain the head position of the patient when in the seated position. The lower shelf 246 may be rotatable and/or translatable, either manually or automatically to accommodate a patient in a number of different positions (for example, standing and sitting at various positions about the column 214).

With reference to FIG. 12, the lower shelf 246 may include a second shelf structure 252 (for example, arm). The second shelf structure 252 may be an arm that extends, for example, parallel to the upper and lower shelves 226, 246 and includes an electronic input device 278 mounted thereto. The electronic input device 278 may be a tablet or computer with an input device, for example a touch screen, a mouse, a keypad, or the like. The electronic input device 278 may be fixed to the second shelf structure 252 or may be removable for wireless communication with the remainder of the imaging system 210. The input device 278 communicates with a controller (for example a controller like controller 54 FIG. 1), or may otherwise be used in place of a controller. The input device 278 allows the operator to input desired changes to the imaging system 210, for example including extending or retracting the column 214, rotating one of the upper and lower shelves 226, 246, rotating or translating the rotating part 230, translating the chair 266 relative to the column 214, or adjusting the height of the chair 266. Further, the operator can control actuations and settings (for example, intensity, focus, etc.) of the X-ray source 238, and, if the X-ray imaging system 210 is provided with multiple X-ray imaging sources, can toggle between the various sources. Further, the input device 278 may provide outputs for the operator, for example status readings of the settings of the X-ray source 238, or results of the scan. In some embodiments the input device 278 may allow choosing of imaging modes and imaging parameters.

With reference to FIG. 15, instead of including a rotatably lower shelf 246, the lower shelf 246 may instead be rotationally fixed to the housing 222. Additionally, while the illustrated lower shelf 246 is shown coupled to the housing 222, the lower shelf 246 may instead be coupled (for example rotatably coupled or fixed) directly to the column 214.

With reference to FIG. 16, the lower shelf 246 may additionally or alternatively rotate (for example, pivot) vertically, such that the lower shelf 46 may be flipped up and tucked adjacent the housing 22 when not in use (for example, via a hinge or joint on the lower shelf 246). Thus, at least a portion of the lower shelf 246 may rotate about not only about the third rotational direction R3 (for example, horizontal rotation), but also about a fourth rotational direction R4 (for example, vertical rotation). Use of the third and/or fourth rotational directions R3, R4 provides space savings within a room, allowing an operator or patient more room (for example, for operator movement or for equipment movement) when the lower shelf 246 is not being used.

The aspects of the X-ray imaging systems 10, 110, and 210 described herein may be used in conjunction with one another and in various combinations. For example, the X-ray imaging systems 10 and 210 may include a frame 118 like that illustrated for the imaging system 110. The X-ray imaging systems 10 and 110 may include a lower shelf 246 and/or head support 250 like that illustrated for the X-ray imaging system 210. The X-ray imaging systems 110 and 210 may include a cephalometric arm 74 like that illustrated for the X-ray imaging system 10. The imaging systems 10 and 110 may include fixed lower shelves 246 as in FIG. 15, or lower shelves 246 that may be pivoted and rotated up against the column as in FIG. 16.

With reference to FIGS. 1-16, the X-ray imaging systems described herein may be used to conduct at least one of computed tomography, panoramic, and cephalometric imaging when a patient is sitting or standing. For example, and with reference to FIG. 1, to obtain a computed tomography image a patient may be sitting on the chair 66. To obtain the computed tomography image, the first X-ray source 38 may be activated, emitting an X-ray beam that is shaped by the beam limiting device 44 and sent to the detector unit 42. The rotating part 30 may rotate around the patient's head (for example 180 degrees), capturing multiple images from different angles. With reference to FIGS. 3 and 4, to obtain a panoramic image, the patient may be standing. The first X-ray source 38 may again be activated, emitting an X-ray beam that is shaped by the beam limiting device 44 and sent to the detector unit 42. The rotating part 30 may move the X-ray source 38 and the detector unit 42 along a particular path that produces a flat two-dimensional image of the curved jaw structure. With reference to FIG. 5, to obtain the cephalometric image, the patient again may be standing (for example in a different location). The second X-ray source 86 may be activated, emitting an X-ray beam that is shaped by the second beam limiting device 90 and sent to the collimator 94 and on to the detector unit 42.

Various features, aspects, and embodiments are set forth in the following claims.

What is claimed is:

1. An X-ray dental imaging system for medical imaging, the X-ray imaging system comprising:
   a column;
   a housing coupled to the column; and
   a lower shelf movably coupled to at least one of the column or the housing, wherein the lower shelf is rotatable from a first position for a seated patient to a second position for a standing patient, wherein the lower shelf includes a first support structure for supporting and positioning the seated patient, and a second support structure for supporting and positioning the standing patient.

2. The X-ray dental imaging system of claim 1, wherein the lower shelf is rotatably coupled to the housing.

3. The X-ray dental imaging system of claim 1, wherein the lower shelf is rotatably coupled to the column.

4. The X-ray dental imaging system of claim 1, wherein the X-ray imaging system is configured such that at least one same imaging mode may be used at each of the first and second positions, and such that the same imaging mode may be taken of both the seated patient and the standing patient.

5. The X-ray dental imaging system of claim 4, wherein the at least one same imaging mode includes a panoramic imaging mode and a computed tomography imaging mode.

6. The X-ray dental imaging system of claim 1, wherein the first support structure includes a head rest to support a back of the seated patient's head in the first position, wherein the X-ray dental imaging system includes a chair, and wherein the head rest is configured to be rotated to a position above the chair in the first position.

7. The X-ray dental imaging system of claim 1, wherein the second support structure includes a handle configured to be held by the standing patient in the second position.

8. The X-ray imaging system of claim 1, wherein the lower shelf includes an arm having a first end rotatably coupled to the housing and a second, distal end disposed opposite the first end, wherein each of the first support structure and the second support structure extends from the second end of the arm.

9. The X-ray dental imaging system of claim 1, wherein the first support structure includes a non-planar head support element that is generally curved to correspond to a profile of the seated patient's head.

10. The X-ray dental imaging system of claim 1, wherein the X-ray imaging system is configured to conduct a computed tomography X-ray image in the first position and a panoramic X-ray image in the second position.

11. The X-ray dental imaging system of claim 1, wherein the lower shelf is adjustable linearly along the column.

12. The X-ray dental imaging system of claim 1, wherein the lower shelf is configured to flip up and tuck adjacent the housing.

13. The X-ray dental imaging system of claim 1, further comprising a frame coupled to the column, wherein the column is rigidly fixed to the frame and extends vertically, wherein the system includes an upper shelf rotatably coupled to the column about a first rotational axis, wherein the upper shelf is adjustable linearly along a length of the column, wherein a rotating part is rotatably coupled to the upper shelf about a second rotational axis spaced from the first rotational axis, wherein the rotating part includes both an X-ray source and a detector unit, wherein the X-ray source and the detector unit provide data for at least one of a panoramic, computed tomography, or cephalometric image, wherein the system includes a chair rigidly fixed to the frame and spaced from the column, and wherein the rotating part is adjustable to accommodate both the seated patient seated on the chair and the standing patient standing on the frame at a location spaced from the chair.

14. The X-ray dental imaging system of claim 1, wherein the first support structure is different than the second support structure.

15. The X-ray dental imaging system of claim 1, wherein the first support structure includes a head support that extends upwardly from an end of the lower shelf, wherein the head support has a curved profile and a first side of the head support is configured to support a back of the seated patient's head in the first position, wherein the second support structure includes a handle that extends downwardly from the end of the lower shelf, wherein the standing patient is configured to hold the handle.

16. The X-ray dental imaging system of claim 15, wherein the second support structure additionally includes a chin block extending upwardly from the second end of the lower shelf, wherein the chin block is configured to support the standing patient's chin.

17. The X-ray dental imaging system of claim 15, wherein the second support structure additionally includes the first side of the head support, wherein the first side of the head support is configured to support a forehead of the standing patient.

18. The X-ray dental imaging system of claim 15, further comprising a chair, wherein a portion of the handle is configured to be rotated to a position behind the chair in the first position.

* * * * *